(12) United States Patent
Okochi et al.

(10) Patent No.: US 8,865,217 B2
(45) Date of Patent: Oct. 21, 2014

(54) ORAL PREPARATION COMPRISING PIOGLITAZONE

(75) Inventors: Kazuhiro Okochi, Osaka (JP); Hiroyoshi Koyama, Osaka (JP); Arisa Maeda, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 1202 days.

(21) Appl. No.: 12/227,572

(22) PCT Filed: May 22, 2007

(86) PCT No.: PCT/JP2007/060756
§ 371 (c)(1),
(2), (4) Date: Nov. 21, 2008

(87) PCT Pub. No.: WO2007/136129
PCT Pub. Date: Nov. 29, 2007

(65) Prior Publication Data
US 2010/0136122 A1    Jun. 3, 2010

(30) Foreign Application Priority Data

May 23, 2006    (JP) .................................. 2006-143390

(51) Int. Cl.
| | | |
|---|---|---|
| *A61K 9/14* | (2006.01) | |
| *A61K 31/4439* | (2006.01) | |
| *A61K 9/20* | (2006.01) | |
| *A61K 9/00* | (2006.01) | |

(52) U.S. Cl.
CPC ........... *A61K 9/0095* (2013.01); *A61K 31/4439* (2013.01); *A61K 9/2009* (2013.01); *A61K 9/0056* (2013.01); *A61K 9/2077* (2013.01)
USPC ........................................................ 424/489

(58) Field of Classification Search
USPC ........................................................ 424/489
See application file for complete search history.

(56) References Cited

U.S. PATENT DOCUMENTS

| 7,135,485 B2 * | 11/2006 | Wizel et al. ................ 514/342 |
| 2002/0114844 A1 * | 8/2002 | Hanna et al. ................ 424/490 |
| 2003/0220374 A1 * | 11/2003 | Needleman ................ 514/342 |
| 2004/0033258 A1 * | 2/2004 | Koike ........................... 424/465 |
| 2005/0131027 A1 * | 6/2005 | Samburski et al. ........... 514/340 |
| 2007/0196435 A1 * | 8/2007 | Higuchi et al. ............... 424/439 |

FOREIGN PATENT DOCUMENTS

| EP | 1 329 217 A1 | 7/2003 |
| EP | 1 757 603 A1 | 2/2007 |
| JP | 7-165572 A | 6/1995 |
| JP | 07165572 A * | 6/1995 |
| JP | 2003-183162 A | 7/2003 |
| WO | WO 02/30400 A1 | 4/2002 |
| WO | WO 03/075919 A1 | 9/2003 |
| WO | WO 03/080056 A2 | 10/2003 |
| WO | WO 2004/026241 A2 | 4/2004 |
| WO | WO 2005/108396 A1 | 11/2005 |
| WO | WO 2007/072992 A2 | 6/2007 |
| WO | WO 2007/126136 A2 | 11/2007 |

OTHER PUBLICATIONS

Sohi et al (Drug Development and Industrial Pharmacy 2004 30:5, 429-448).*
Breslin et al., "Salt enhances flavour by suppressing bitterness," Nature, Jun. 5, 1997, 387:563-4.
Nakamura et al., "The Effect of Various Substances on the Suppression of the Bitterness of Quinine—Human Gustatory Sensation, Binding, and Taste Sensor Studies," Chem. Pharm. Bull., 2002, 51(12):1589-1593.
Ogawa et al., "The Combination Effect of L-Arginine and NaCl on Bitterness Suppression of Amino Acid Solutions," Chem. Pharm. Bull., 2004, 52(2):172-177.
Iyakuhin Tenkabutsu Jiten (Japanese Encyclopedia of Pharmaceutical Additives), 1994, 20 (see relevance discussion in IDS Transmittal).
Pansporin T tablet drug label information, 1990 (see relevance discussion in IDS Transmittal).

* cited by examiner

*Primary Examiner* — Benjamin Packard
(74) *Attorney, Agent, or Firm* — Foley & Lardner LLP

(57) ABSTRACT

The present invention provides an oral preparation sufficiently masking the bitter taste of pioglitazone and a salt thereof. The present invention provides an oral preparation containing pioglitazone or a salt thereof and alkali metal chloride.

12 Claims, No Drawings

ORAL PREPARATION COMPRISING PIOGLITAZONE

TECHNICAL FIELD

The present invention relates to an oral preparation suppressing the bitter taste of pioglitazone or a salt thereof, which comprises pioglitazone or a salt thereof and alkali metal chloride.

BACKGROUND OF THE INVENTION

Pioglitazone and a salt thereof give a bitter taste for those having a normal sense of taste.

As a preparation masking the unpleasant taste, particularly an unpleasant taste of a pharmaceutical ingredient having a bitter taste, the following preparations have been reported.

A solid preparation containing 1) a basic medicinal component having an unpleasant taste, 2) a saccharide, 3) a polyanionic polymer, 4) a corrigent and 5) carboxymethylcellulose (see patent reference 1); and an ecabet sodium-containing oral preparation containing ecabet sodium and alkali chloride as a bitter taste masking agent (see patent reference 2).

Patent reference 1: WO 02/30400
Patent reference 2: JP-A-H7-165572

DISCLOSURE OF THE INVENTION

For a pharmaceutical product with high administration compliance of patients, the development of an oral preparation (to be specific, a solid preparation) sufficiently masking the bitter taste of pioglitazone or a salt thereof has been desired.

Particularly, since a preparation disintegrating in the oral cavity is used for administration by intraoral disintegration in a short time, the bitter taste of pioglitazone and a salt thereof is desired to be sufficiently masked.

The present inventors have studied the formulation of pioglitazone and a salt thereof having a bitter taste, and found that a combined use of pioglitazone or a salt thereof with alkali metal chloride affords an oral preparation sufficiently masking the bitter taste of pioglitazone and a salt thereof. Such finding is surprising to those of ordinary skill in the art. To be specific, according to the finding of the present inventors, alkali metal chlorides do not exhibit a bitter taste suppressing effect for, for example, cefotiam hexetil hydrochloride and fursultiamine hydrochloride having a similar bitter taste, and exhibit an extremely weak bitter taste suppressing effect for metformin, and a particularly remarkable bitter taste suppressing effect for pioglitazone and a salt thereof.

Accordingly, the present invention provides the following.
(1) An oral preparation comprising pioglitazone or a salt thereof, and alkali metal chloride (hereinafter sometimes to be abbreviated as the oral preparation of the present invention).
(2) The preparation of the above-mentioned (1) wherein the alkali metal chloride is sodium chloride.
(3) The preparation of the above-mentioned (1) wherein the alkali metal chloride is contained in about 1-about 500 parts by weight relative to 100 parts by weight of the pioglitazone or a salt thereof.
(4) The preparation of the above-mentioned (1) which is a tablet.
(5) The preparation of the above-mentioned (4) wherein the tablet is a tablet disintegrating in the oral cavity.
(6) The preparation of the above-mentioned (1) wherein the bitter taste of pioglitazone or a salt thereof is suppressed.
(7) The preparation of the above-mentioned (1) comprising coated particles wherein particles comprising pioglitazone or a salt thereof are coated with saccharide.
(8) A bitter taste suppressing agent of pioglitazone or a salt thereof, which comprises alkali metal chloride.
(9) Use of alkali metal chloride for suppressing the bitter taste of pioglitazone or a salt thereof.

Effect of the Invention

The oral preparation of the present invention can be administered very easily since the bitter taste of pioglitazone and a salt thereof is sufficiently masked, and therefore, is useful as a pharmaceutical product with high administration compliance of patients. Moreover, the oral preparation of the present invention can be easily produced by combining pioglitazone or a salt thereof and alkali metal chloride.

When the oral preparation of the present invention is an oral preparation rapidly disintegrating in the oral cavity, the preparation is extremely useful as a pharmaceutical product with high administration compliance of patients having difficulty in swallowing pharmaceutical agents, such as the elderly and children, and the like, since the bitter taste of pioglitazone and a salt thereof is sufficiently masked and the preparation has superior disintegratability in the oral cavity. Moreover, the oral preparation rapidly disintegrating in the oral cavity shows superior properties of appropriate preparation strength, long-term preservation stability and the like.

The present invention is explained in detail in the following.

For "pioglitazone or a salt thereof" used for the oral preparation of the present invention, as the salt of pioglitazone, pharmacologically acceptable salts, for example, salts with inorganic acid, salts with organic acid, salts with acidic amino acid and the like can be mentioned.

Preferable examples of the salts with inorganic acid include salts with hydrochloric acid, hydrobromic acid, nitric acid, sulfuric acid, phosphoric acid and the like.

Preferable examples of the salts with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salts with acidic amino acid include salts with aspartic acid, glutamic acid and the like.

Pioglitazone or a salt thereof is preferably pioglitazone hydrochloride.

Pioglitazone and a salt thereof may be diluted with a diluent and the like that are generally used for medical field, food field and the like.

The median size of pioglitazone and a salt thereof is preferably 0.5 to 25 µm, more preferably 1 to 21 µm, particularly preferably 1 to 10 µm. By employing such median size, an oral preparation of pioglitazone or a salt thereof, which is superior in the dissolution property, can be obtained.

The above-mentioned preferable median size is applied to pioglitazone or a salt thereof used as the starting material for producing the oral preparation of the present invention [including a pulverized product obtained by pulverization during the process of producing an oral preparation, a mixed pulverized product obtained by pulverization together with an excipient (e.g., crystalline cellulose) and the like]. That is, the median size of pioglitazone or a salt thereof may change during a production process of the oral preparation of the present invention, or a preservation process of the oral preparation after production, by coagulation of pioglitazone or a salt thereof and the like. The pulverization is performed using a preparation forming machine such as a mortar, a jet mill, a hammer mill, a screen mill (P-3; Showa Kagaku Kikai Kosakusho Co., Ltd.) and the like.

In the present specification, the median size means a particle size that divides into crude particles and fine granules by 50% based on the weight distribution or number distribution. The median size can be measured, for example, by laser diffraction particle size distribution measurement apparatus (e.g., SYNPATEC HELOS-RODOS particle distribution apparatus).

The dispersibility of pioglitazone or a salt thereof having the above-mentioned desired median size is preferably that "not more than 10% of the total amount is particles having not more than 0.1 µm and not more than 10% of the total amount is particles having not less than 1000 µm".

While the content of pioglitazone or a salt thereof in the oral preparation of the present invention varies depending on the dosage form, dose and the like of the oral preparation, when the oral preparation is a solid preparation, it is generally 0.01-60 parts by weight, preferably 0.01-40 parts by weight, per 100 parts by weight of the solid oral preparation. When it is a liquid preparation, the content is generally 0.01-30 parts by weight, more preferably 0.01-20 parts by weight, per 100 parts by weight of the liquid oral preparation.

The alkali metal of the "alkali metal chlorides" to be used for the oral preparation of the present invention is, for example, lithium, sodium, potassium and the like, and the "alkali metal chloride" is preferably sodium chloride and potassium chloride, particularly preferably sodium chloride.

The average particle size of the "alkali metal chloride" when contained in a solid preparation is generally 0.1-1000 µm, preferably 1-500 µm, more preferably 5-150 µm. The average particle size is measured by, for example, a laser diffraction particle size distribution measurement apparatus (e.g., SYNPATEC HELOS-RODOS particle distribution apparatus). Particularly, an average particle size of not more than 500 µm is preferable, since alkali metal chloride is not localized in the oral preparation of the present invention, and the bitter taste of "pioglitazone or a salt thereof" can be effectively masked and the roughness of alkali metal chloride is not caused intraorally during administration of the oral preparation of the present invention.

The "alkali metal chloride" to be used in the present invention is preferably obtained by pulverization of commercially available "alkali metal chloride".

Here, pulverization is performed using a preparation forming machine, such as a mortar, a jet mill, a hammer mill, a screen mill (P-3; Showa Kagaku Kikai Kosakusho Co., Ltd.) and the like.

While the content of alkali metal chloride in the oral preparation of the present invention varies depending on the kind and the like of the alkali metal chloride, it is generally 0.05-40 parts by weight, preferably 0.1-30 parts by weight, per 100 parts by weight of the solid oral preparation. It is 0.05-5 parts by weight, preferably 0.05-3 parts by weight, per 100 parts by weight of the liquid oral preparation.

In addition, the amount of alkali metal chloride in the oral preparation of the present invention is preferably 1-500 parts by weight, more preferably 2-250 parts by weight, per 100 parts by weight of pioglitazone or a salt thereof.

The oral preparation of the present invention may contain additives conventionally used in the preparation technical field. As the additive, for example, excipient, disintegrant, binder, lubricant, coloring agent, pH regulator, surfactant, stabilizer, corrigent, sweetener, flavor, fluidizing agent, liquid medium and the like can be used. These additives are used in an amount conventionally employed in the preparation technical field. In addition, these additives may be used in a mixture of two or more kinds thereof in an appropriate rate.

As the excipient, for example, saccharides; crystalline cellulose; starches such as corn starch, potato starch, wheat starch, rice starch, partly pregelatinized starch, pregelatinized starch, porous starch and the like; anhydrous calcium phosphate, precipitated calcium carbonate, calcium silicate and powder cellulose can be used.

As the saccharides, for example, sugar, starch sugar, lactose, honey and sugar alcohol can be used. Two or more kinds of these saccharides may be used in a mixture in an appropriate ratio.

As the sugar, for example, sucrose, glycosyl sucrose [coupling sugar (trade name)], fructooligosaccharide and palatinose can be used.

As the starch sugar, for example, glucose, maltose, powdered starch syrup, starch syrup and fructose can be used.

As the lactose, for example, lactose, isomerized lactose (lactulose) and reduction lactose (lactitol) can be used.

As the honey, various kinds of honey generally used for eating can be used.

As the sugar alcohol, for example, sorbitol, D-mannitol, is maltitol, hydrogenated glucose syrup, xylitol, reduced paratinose, erythritol and trehalose can be used.

The saccharides are preferably sugar alcohol and lactose, more preferably D-mannitol and lactose.

The content of the saccharides in the oral preparation is, for example, 10-90 parts by weight, preferably 40-85 parts by weight, per 100 parts by weight of the oral preparation.

Using 1-20 parts by weight, preferably 2-10 parts by weight, of the saccharides, per 1 part by weight of pioglitazone or a salt thereof, the bitter taste of pioglitazone or a salt thereof can be more effectively masked.

As crystalline cellulose, for example, CEOLUS KG801, KG802, PH101, PH102, PH301, PH302, PH-F20, RC-A591NF (trade name, manufactured by Asahi Kasei Chemicals Corporation) can be used. It also includes microcrystalline cellulose. Using crystalline cellulose, an oral preparation having appropriate preparation strength, which is superior in rapid disintegratability in the oral cavity, can be obtained.

The content of crystalline cellulose in the oral preparation is, for example, 0.1-50 parts by weight, preferably 0.5-40 parts by weight, particularly preferably 1-25 parts by weight, per 100 parts by weight of the oral preparation.

As the disintegrant, for example, carboxymethylcellulose, calcium carboxymethylcellulose (carmellose calcium), sodium carboxymethyl starch, croscarmellose sodium, crospovidone [preferably, Kollidon CL, CL-M, CL-F, CL-SF (trade name, BASF JAPAN LTD.); Polyplasdone XL, XL-10, INF-10 (trade name, ISP JAPAN LTD.)], low-substituted hydroxypropylcellulose [preferably low-substituted hydroxypropylcellulose having a hydroxypropoxyl group content of 5-16 wt %, such as LH11, LH21, LH31, LH22, LH32, LH20, LH30, LH32, LH33 (trade name, manufactured by Shin-Etsu Chemical Co., Ltd.) and the like], and hydroxypropyl starch can be used. Particularly, crospovidone is preferable, and Kollidon CL, CL-F, CL-SF (trade name, BASF JAPAN LTD.); and Polyplasdone XL (trade name, ISP JAPAN LTD.) are preferable. Using crospovidone, an oral preparation superior in rapid disintegratability in the oral cavity can be obtained.

The content of the disintegrant in the oral preparation is, for example, 0.5-25 parts by weight, preferably 1-15 parts by weight, per 100 parts by weight of the oral preparation.

As the binder, for example, hydroxypropylcellulose [preferably HPC-SSL, SL, L (trade name, NIPPON SODA CO., LTD.)], hydroxypropylmethylcellulose, povidone (polyvinylpyrrolidone) and gum arabic powder can be used. Of these, hydroxypropylcellulose is preferable.

As the lubricant, for example, magnesium stearate, calcium stearate, talc, sucrose esters of fatty acids and sodium stearyl fumarate can be used. Of these, magnesium stearate is preferable.

As the coloring agent, for example, foodcolors such as Food Yellow No. 5 (Sunset Yellow, same as Food yellow No. 6 in the US), Food Red No. 2, Food Blue No. 2 and the like, food lake colors and yellow ferric oxide can be used.

As the pH regulator, for example, citrate, phosphate, carbonate, tartrate, fumarate, acetate and amino acid salt can be used.

As the surfactant, for example, sodium lauryl sulfate, polysorbate 80, polyoxyethylene (160) polyoxypropylene (30) glycol, polyoxyethylene (196) polyoxypropylene (67) glycol and polyoxyethylene hydrogenated castor oil 60 can be used.

As the stabilizer, for example, sodium ascorbate, tocopherol, tetrasodium edetate, nicotinamide, cyclodextrins; alkaline earth metal salts (e.g., calcium carbonate, calcium hydroxide, magnesium carbonate, magnesium hydroxide, magnesium silicate, magnesium aluminate) and butylhydroxyanisole can be used.

As the corrigent, for example, ascorbic acid, (anhydrous) citric acid, tartaric acid and malic acid can be used.

As the sweetener, for example, aspartame, acesulfame potassium, thaumatin, saccharin sodium and dipotassium glycyrrhizinate can be used. Of these, aspartame is preferable.

As the flavor, for example, menthol, peppermint oil, lemon oil and vanillin can be used.

As the fluidizing agent, for example, light anhydrous silicic acid and hydrated silicon dioxide can be mentioned. Here, the light anhydrous silicic acid may be any containing hydrated silicon dioxide ($SiO_2 \cdot nH_2O$) (n is an integer) as a main component and, as concrete examples thereof, Sylysia 320 (trade name, FUJI SILYSIA CHEMICAL LTD.), AEROSIL 200 (trade name, NIPPON AEROSIL CO., LTD.) and the like can be used.

As the liquid medium, water, ethanol, macrogol 400, propylene glycol, glycerol, concentrated glycerin and the like can be used.

When the above-mentioned various additives are solids, the particle size of the additives is preferably not more than 500 μm, which does not easily cause roughness in the oral cavity.

As the dosage form of the oral preparation of the present invention, for example, solid preparations and liquid preparations can be mentioned. As the solid preparations, for example, tablet, capsule, powder, granule, troche and the like can be mentioned. Of these, tablet is preferable.

The shape of the oral preparation is not particularly limited, and may be any of round, caplet, doughnut, oblong and the like.

The oral preparation may be coated with a coating agent, and may have a mark and letters for identification and further a score line for partition.

As the coating base, for example, sugar coating base, water-soluble film coating base, enteric film coating base, sustained-release film coating base and the like can be used.

As the sugar coating base, sucrose is used and one or more kinds selected from talc, precipitated calcium carbonate, gelatin, gum arabic, pullulan, carnauba wax and the like may be used in combination.

As the water-soluble film coating base, for example, cellulose polymers such as hydroxypropylcellulose, hydroxypropylmethylcellulose, hydroxyethylcellulose, methylhydroxyethylcellulose and the like; synthetic polymers such as polyvinylacetal diethylaminoacetate, aminoalkyl methacrylate copolymer E [Eudragit E (trade name)], polyvinylpyrrolidone and the like; polysaccharides such as pullulan and the like; and the like can be used.

As the enteric film coating base, for example, cellulose polymers such as hydroxypropylmethylcellulose phthalate, hydroxypropylmethylcellulose acetatesuccinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D55 (trade name)], methacrylic acid copolymer S [Eudragit S (trade name)] and the like; naturally occurring substances such as shellac and the like; and the like can be used.

As the sustained-release film coating base, for example, cellulose polymers such as ethylcellulose, cellulose acetate and the like; acrylic acid polymers such as aminoalkyl methacrylate copolymer RS [Eudragit RS (trade name)], ethyl acrylate-methyl methacrylate copolymer suspension [Eudragit NE (trade name)] and the like; and the like can be used.

Two or more kinds of the above-mentioned coating bases may be used in a mixture in an appropriate ratio. In addition, a coating additive may also be used during coating.

As the coating additive, for example, light masking agents and/or coloring agents such as titanium oxide, talc, ferric oxide and the like; plasticizers such as polyethylene glycol, triethyl citrate, castor oil, polysorbates and the like; organic acids such as citric acid, tartaric acid, malic acid, ascorbic acid and the like; and the like can be used.

As the liquid preparation, liquid, suspension, syrup, injection and the like can be used.

The oral preparation of the present invention can be produced using the above-mentioned various additives according to a method conventionally used in the preparation technical field.

Specifically, the oral preparation of the present invention can be produced by mixing pioglitazone or a salt thereof, and alkali metal chloride with the above-mentioned various additives and, where necessary, compression-molding the mixture.

The mixing (including granulation, drying, milling and the like) is performed, for example, using a preparation forming machine such as a V-type mixer, a tumbler mixer, a high speed agitating granulator (FM-VG-10; POWREX CORPORATION), an all-round kneader (Hata Tekkosho, Co., Ltd.), a fluidized bed granulation dryer (LAB-1, FD-3S, FD-3SN; POWREX CORPORATION), a box vacuum dryer (Kusunoki Machinery Co., Ltd.), a screen mill (P-3; Showa Kagaku Kikai Kosakusho Co., Ltd.) and the like.

The compression-molding is performed, for example, by punching generally at a pressure of 3-35 kN/cm$^2$ using a single-punch tableting machine (KIKUSUI SEISAKUSHO LTD.), a rotary tableting machine (KIKUSUI SEISAKUSHO LTD.), Auto-graph (Shimadzu Corporation) and the like.

The oral preparation of the present invention is preferably a solid preparation rapidly disintegrating in the oral cavity (preferably a tablet disintegrating in the oral cavity). Here, the property "rapidly disintegrating in the oral cavity" means disintegration of a solid preparation in the oral cavity in a short time (e.g., 5-90 sec). While the disintegration time in the oral cavity of the solid preparation rapidly disintegrating in the oral cavity (time necessary for a solid preparation to be completely disintegrated with the saliva in the oral cavity of healthy adult male and female) varies depending on the dosage form, size and the like of the solid preparation, when the solid preparation is a tablet, it is, for example, generally about 5-90 sec, preferably 5-60 sec, more preferably 5-30 sec.

The solid preparation rapidly disintegrating in the oral cavity is useful for the prophylaxis or treatment of various diseases as a preparation easily administered to patients having difficulty in swallowing pharmaceutical agents, such as the elderly and children, or a safe preparation for general adults in the time of emergency.

The hardness of the oral preparation of the present invention (measurement value by tablet hardness tester) is about preferably 15-200 N, more preferably 15-150 N.

Specific preferable examples of the oral preparation of the present invention include the following preparation (1) and preparation (2).

Preparation (1):

An oral preparation comprising pioglitazone or a salt thereof, and alkali metal chloride, which comprises coated particles wherein particles comprising pioglitazone or a salt thereof are coated with saccharide.

That is, preparation (1) is, of the oral preparations of the present invention, a preparation wherein pioglitazone or a salt thereof contained in the oral preparation is present in the state of "coated particles wherein particles comprising pioglitazone or a salt thereof are coated with saccharide", where alkali metal chloride may be contained inside or outside the coated particles.

As the saccharide employed in the "coated particles wherein particles comprising pioglitazone or a salt thereof are coated with saccharide", those exemplified as the aforementioned additives can be used. Of these, lactose is preferable. The content of the saccharide is, for example, 5-80 parts by weight, preferably 10-50 parts by weight, per 100 parts by weight of preparation (1).

With regard to preparation (1), the "particles comprising pioglitazone or a salt thereof" (sometimes to be abbreviated as "the particles of the present invention" in the present specification) can be produced by granulating pioglitazone or a salt thereof with an additive as necessary. After granulation, where necessary, an operation such as drying, milling and the like may be performed.

The additive is preferably an excipient (e.g., crystalline cellulose, lactose), a disintegrant (e.g., calcium carboxymethylcellulose), a binder (e.g., hydroxypropylcellulose), a coloring agent (e.g., yellow ferric oxide) and the like.

The content of pioglitazone or a salt thereof in the particles of the present invention is preferably 0.1-60 parts by weight, more preferably 1-40 parts by weight, per 100 parts by weight of the particles of the present invention.

The content of the particles of the present invention in preparation (1) is, for example, 1-100 parts by weight, preferably 5-90 parts by weight, per 100 parts by weight of the preparation (1).

The particles of the present invention are preferably particles consisting of pioglitazone or a salt thereof (preferably pioglitazone hydrochloride), an excipient (preferably crystalline cellulose and lactose), a disintegrant (preferably calcium carboxymethylcellulose) and a binder (preferably hydroxypropylcellulose), and optionally further containing a coloring agent (preferably yellow ferric oxide).

The particles of the present invention is more preferably a granulation product obtained by granulating pioglitazone or a salt thereof (preferably pioglitazone hydrochloride), an excipient (preferably crystalline cellulose and lactose) and a disintegrant (preferably calcium carboxymethylcellulose) with a solvent (preferably water) dispersion of a binder (preferably hydroxypropylcellulose) and a coloring agent (preferably yellow ferric oxide). A coloring agent may be omitted from the granulation product.

The above-mentioned dispersion may be any of a solution and a suspension, and the "dispersion" in the present specification encompasses both the solution and the suspension.

The "coated particles wherein particles comprising pioglitazone or a salt thereof are coated with saccharide" (sometimes to be abbreviated as "the coated particles of the present invention" in the present specification) contained in preparation (1) can be produced by coating the particles of the present invention with saccharide together with additive as necessary.

The additive is preferably a binder (e.g., hydroxypropylcellulose), a coloring agent (e.g., yellow ferric oxide) and the like.

The coated particles of the present invention include not only coated particles wherein the particles of the present invention are completely (100% of the entire surface area of the particles of the present invention) coated with saccharide, but also coated particles wherein the particles of the present invention are partially (not less than 30%, preferably not less than 50%, of the entire surface area of the particles of the present invention) coated with saccharide.

The content of coated particles of the present invention in preparation (1) is, for example, 1-100 parts by weight, preferably 5-90 parts by weight, per 100 parts by weight of preparation (1).

The coated particles of the present invention are preferably coated particles consisting of pioglitazone or a salt thereof (preferably pioglitazone hydrochloride), an excipient (preferably crystalline cellulose and lactose), a disintegrant (preferably calcium carboxymethylcellulose), a binder (preferably hydroxypropylcellulose) and saccharide (preferably lactose), and optionally further containing a coloring agent (preferably yellow ferric oxide).

The coated particles of the present invention are more preferably 1) a granulation product obtained by granulating pioglitazone or a salt thereof (preferably pioglitazone hydrochloride), an excipient (preferably crystalline cellulose and lactose) and a disintegrant (preferably calcium carboxymethylcellulose) with a solvent (preferably water) dispersion of saccharide (preferably lactose), a binder (preferably hydroxypropylcellulose) and a coloring agent (preferably yellow ferric oxide);

2) a granulation product obtained by granulating pioglitazone or a salt thereof (preferably pioglitazone hydrochloride), an excipient (preferably crystalline cellulose and lactose) and a disintegrant (preferably calcium carboxymethylcellulose) successively with a solvent (preferably water) dispersion of a binder (preferably hydroxypropylcellulose) and a coloring agent (preferably yellow ferric oxide) and a solvent (preferably water) dispersion of a binder (preferably hydroxypropylcellulose) and saccharide (preferably lactose);

3) a granulation product obtained by granulating pioglitazone or a salt thereof (preferably pioglitazone hydrochloride), an excipient (preferably crystalline cellulose and lactose) and a disintegrant (preferably calcium carboxymethylcellulose) with a solvent (preferably water) dispersion of a binder (preferably hydroxypropylcellulose) and a coloring agent (preferably yellow ferric oxide), and coating the obtained granulation product with saccharide (preferably lactose); and the like.

The coloring agent may be omitted from the granulation product of the above-mentioned 1), the granulation product of the above-mentioned 2), and the coated particles of the above-mentioned 3).

Preparation (1) can be produced by mixing the coated particles of the present invention with an additive as necessary and compression-molding the mixture as necessary.

The additive is preferably an excipient (e.g., crystalline cellulose and mannitol), a disintegrant (e.g., crospovidone), a sweetener (e.g., aspartame), a lubricant (e.g., magnesium stearate), a coloring agent (e.g., yellow ferric oxide) and the like.

Preparation (1) is preferably a solid preparation consisting of pioglitazone or a salt thereof (preferably pioglitazone hydrochloride), an alkali metal chloride (preferably sodium chloride), an excipient (preferably crystalline cellulose, lactose and mannitol), a disintegrant (preferably calcium carboxymethylcellulose and crospovidone), a binder (preferably hydroxypropylcellulose), saccharide (preferably lactose) and a lubricant (preferably magnesium stearate), and optionally further containing a coloring agent (preferably yellow ferric oxide) and/or a sweetener (preferably aspartame).

Preparation (1) is more preferably a solid preparation (preferably tablet) obtained by mixing one member selected from the granulation product of the above-mentioned 1), the granulation product of the above-mentioned 2) and the coated particles of the above-mentioned 3), with alkali metal chloride (preferably sodium chloride), an excipient (preferably crystalline cellulose and mannitol), a disintegrant (preferably crospovidone), a sweetener (preferably aspartame), a lubricant (preferably magnesium stearate) and a coloring agent (preferably yellow ferric oxide), and compression-molding (preferably tabletting) the obtained mixture. The sweetener and/or the coloring agent may be omitted from the solid preparation.

Preparation (2):

A solid preparation consisting of pioglitazone or a salt thereof (preferably pioglitazone hydrochloride), alkali metal chloride (preferably sodium chloride), an excipient (preferably crystalline cellulose and mannitol), a disintegrant (preferably crospovidone), a binder (preferably hydroxypropylcellulose), saccharide (preferably lactose) and a lubricant (preferably magnesium stearate), and optionally further containing a coloring agent (preferably yellow ferric oxide).

Preparation (2) is preferably a solid preparation (preferably tablet) obtained by granulating pioglitazone or a salt thereof (preferably pioglitazone hydrochloride), an excipient (preferably crystalline cellulose and mannitol) and a disintegrant (preferably crospovidone) with a solvent (preferably water) dispersion of alkali metal chloride (preferably sodium chloride) and a coloring agent (preferably yellow ferric oxide), mixing the obtained granulation product, saccharide (preferably lactose) and a lubricant (preferably magnesium stearate), and compression-molding (preferably tabletting) the obtained mixture. The coloring agent may be omitted from the solid preparation.

In the present specification, the "particles" means those having an almost uniform shape and size afforded by granulating a starting material such as powdery, massive, liquid or molten material and the like by a wet granulation method, a dry granulation method or a heat granulation method. As the "particles", for example, powder, fine granule and granule can be mentioned. These preferably have the particle size defined in the Japanese Pharmacopoeia 14th Edition.

That is, in a particle size test of a preparation, the particle size of powder is preferably that "the whole amount passes through #18 (850 µm) sieve and not more than 5% of the total amount remains on #30 (500 µm) sieve", the particle size of fine granules is preferably, within the aforementioned range of particle size of powder, that "not more than 10% of the total amount passes through #200 (75 µm) sieve", and the particle size of granule is preferably that "the whole amount passes through #10 (1700 µm) sieve, not more than 5% of the total amount remains on #12 (1400 µm) sieve, and not more than 15% of the total amount passes through #42 (355 µm) sieve".

In the present specification, the average particle size of the "particle" is generally 44-2000 µm, preferably 75-1000 µm. As used herein, the average particle size is a value measured by, for example, a laser diffraction particle distribution apparatus (e.g., SYNPATEC HELOS-RODOS particle distribution apparatus).

The "particles" in the present specification may show different shape and size during the preparation process (e.g., compression-molding step) of the oral preparation of the present invention.

Of the oral preparations of the present invention, the above-mentioned preparation (1), particularly preparation (1) containing the granulation product of the above-mentioned 2) or the coated particles of the above-mentioned 3) is preferable because it affords superior effects of superior preservation stability and absence of time-course changes in the preparation quality (e.g., discoloration; time-course changes in the dissolution property of pioglitazone or a salt thereof).

Moreover, since preparation (1) shows superior producibility such as no attachment to a punch or die during tabletting and the like, it is suitable for industrial production.

Furthermore, preparation (1) shows superior property in that its dissolution behavior of pioglitazone or a salt thereof produces only a small variation between respective preparations (e.g., plural tablets).

The oral preparation of the present invention can be safely administered orally to a mammal (e.g., mouse, rat, rabbit, cat, dog, bovine, horse, monkey, human).

While the dose of the oral preparation of the present invention varies depending on the subject of administration, the severity of the disease and the like, it can be selected from the range affording the effective amount of pioglitazone or a salt thereof. The dose of the oral preparation of the present invention is, for example, generally 7.5-60 mg/day, preferably 15-60 mg/day, as pioglitazone for one adult (body weight 60 kg), which may be administered in 2-3 portions a day.

When the oral preparation of the present invention is a solid preparation disintegrating in the oral cavity (preferably orally disintegratable tablet), the solid preparation can be administered without water, or with a suitable amount of water. In addition, the solid preparation can also be administered without disintegration in the oral cavity.

The oral preparation of the present invention is useful, for example, as an agent for the prophylaxis or treatment for the diseases such as diabetes (e.g., type-1 diabetes, type-2 diabetes, gestational diabetes), hyperlipidemia (e.g., hypertriglyceridemia, hypercholesterolemia, hypoHDL-cholesterolemia, postprandial hyperlipidemia), impaired glucose tolerance (IGT), diabetic complications [e.g., neuropathy, nephropathy, retinopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder etc.], obesity, osteoporosis, cachexia (e.g., carcinocachexia, tuberculous cachexia, diabetic cachexia, hemopathic cachexia, endocrinopathic cachexia, infectious cachexia or cachexia induced by acquired immunodeficiency syndrome), fatty liver, hypertension, polycystic ovary syndrome, renal disease (e.g., diabetic nephropathy, glomerulonephritis, glomerulosclerosis, nephrosis syndrome, hypertensive nephrosclerosis, terminal renal disorder), muscular dystrophy, cardiac infarction, angina pectoris, cerebrovascular disorder (e.g., cerebral infarction, cerebral apoplexy), insulin resistance syndrome, Syndrome X, dysmetabolic syndrome, hyperinsulinemia, hyperinsulinemia-induced sensory disorder, tumor (e.g., leukemia, breast cancer, prostate cancer, skin cancer), irritable bowel syndrome, acute or chronic diarrhea, inflammatory disease [e.g., Alzheimer's disease, chronic articular rheumatism, spondylitis deformans, osteoarthritis, lumbago, gout, postoperative or traumatic inflammation, regression of puffiness, neuralgia, pharyngolaryngitis, cystitis, hepatitis (inclusive of nonalcoholic steatohepatitis), pneumonia, pancreatitis, inflammatory colitis, ulcerative colitis], visceral obesity syndrome, arteriosclerosis (e.g., atherosclerosis), multiple sclerosis, sepsis, psoriasis, Parkinson's disease, atopic dermatitis and the like; or secondary prevention of the above-mentioned various diseases (e.g., secondary prevention of cardiovascular event such as cardiac infarction and the like) and suppression of progression (e.g., suppression of progression from impaired glucose tolerance to diabetes, suppression of progression to arteriosclerosis in diabetes patients).

The oral preparation of the present invention can be used in combination with an active ingredient other than pioglitazone or a salt thereof (hereinafter sometimes to be abbreviated as concomitant component). In this case, the time of administration of pioglitazone or a salt thereof and that of the concomitant component are not limited, and they may be administered simultaneously or in a staggered manner to the administration subject. In addition, the oral preparation of the present invention and the concomitant component may be administered to an administration subject as two kinds of preparations each containing the active ingredient, or a single preparation containing the both active ingredients.

The dose of the concomitant component can be appropriately determined based on the dose employed clinically.

Use of the concomitant component in this way provides superior effects such as 1) enhancing the action of the oral preparation of the present invention or the concomitant component (synergistic effect on the action of the pharmaceutical agents), 2) reducing the dose of the oral preparation of the present invention or the concomitant component (effect of reducing the dose of pharmaceutical agents as compared to a single drug administration), 3) reducing the secondary action of the oral preparation of the present invention or the concomitant component, and the like.

As the concomitant component for the oral preparation of the present invention, for example, therapeutic drug for diabetes (excluding pioglitazone or a salt thereof), therapeutic drug for diabetic complications, therapeutic drug for hyperlipidemia, antihypertensive drug, antiobesity drug, diuretic drug, antithrombotic drug and the like can be mentioned. These active ingredients may be low-molecular-weight compounds, or high-molecular-weight protein, polypeptide, antibody, vaccine and the like. In addition, two or more kinds of the active ingredients may be used in a mixture in an appropriate ratio.

As the therapeutic drug for diabetes, for example, insulin preparations [e.g., animal insulin preparations extracted from the pancreas of bovine, swine; human insulin preparations synthesized by genetic engineering using *Escherichia coli* or yeast; zinc insulin; protamine zinc insulin; fragment or derivative of insulin (e.g., INS-1)], α-glucosidase inhibitors (e.g., voglibose, acarbose, miglitol, emiglitate), biguanides [e.g., phenformin, metformin, buformin or a salt thereof (e.g., hydrochloride, fumarate, succinate)], insulin sensitizer (excluding pioglitazone and a salt thereof) (e.g., rosiglitazone or a salt thereof (preferably maleate), reglixane, netoglitazone, rivoglitazone, FK-614, compound described in WO01/38325, tesaglitazar, ragaglitazar, muraglitazar, edaglitazone, naveglitazar, metaglidasen, LY-510929, balaglitazone, T-131 or a salt thereof, THR-0921), insulin secretagogues [e.g., sulfonylurea (e.g., tolbutamide, glibenclamide, gliclazide, chlorpropamide, tolazamide, acetohexamide, glyclopyramide, glimepiride, glipizide, glybuzole), non-sulfonylurea insulin secretagogues (e.g., repaglinide, nateglinide, mitiglinide or calcium salt hydrate thereof)], GLP-1 receptor agonists [e.g., GLP-1, GLP-1MR agent, NN-2211, exendin-4, BIM-51077, Aib(8,35)hGLP-1(7,37)NH$_2$, CJC-1131], dipeptidyl-peptidase IV inhibitors (e.g., vildagliptin, saxagliptin, NVP-DPP-278, PT-100, NVP-DPP-728, P32/98, P93/01, TS-021, sitagliptin, denagliptin, T-6666), β3 agonists (e.g., AJ-9677), amylin agonists (e.g., pramlintide), phosphotyrosine phosphatase inhibitors (e.g., sodium vanadate), gluconeogenesis inhibitor (e.g., glycogen phosphorylase inhibitor, glucose-6-phosphatase inhibitor, glucagon antagonist), SGLUT (sodium-glucose cotransporter) inhibitors (e.g., T-1095), 11β-hydroxysteroid dehydrogenase inhibitors (e.g., BVT-3498), adiponectin or agonist thereof, IKK inhibitors (e.g., AS-2868), leptin resistance-improving drug, somatostatin receptor agonists (e.g., compounds described in WO01/25228, WO03/42204, WO98/44921, WO98/45285, WO99/22735), glucokinase activators (e.g., Ro-28-1675), GPR40 agonist, GIP (glucose-dependent insulinotropic peptide) and the like can be mentioned.

As the therapeutic drug for diabetic complications, for example, aldose reductase inhibitors (e.g., tolrestat, epalrestat, zenarestat, zopolrestat, minalrestat, fidarestat, CT-112, ranirestat), neurotrophic factors (e.g., NGF, NT-3, BDNF), neurotrophic factor production-secretion promoters [e.g., neurotrophin production-secretion promoters described in WO01/14372 (e.g., 4-(4-chlorophenyl)-2-(2-methyl-1-imidazolyl)-5-(3-(2-methylphenoxy)propyl)oxazole)], PKC inhibitors (e.g., ruboxistaurin mesylate), AGE inhibitors (e.g., ALT946, pimagedine, pyratoxanthine, N-phenacylthiazolium bromide (ALT766), EXO-226, ALT-711, pyridorin, pyridoxamine), active oxygen scavengers (e.g., thioctic acid), cerebral vasodilators (e.g., tiapuride, mexiletine), somatostatin receptor agonists (e.g., BIM23190) and apoptosis signal regulating kinase-1 (ASK-1) inhibitors can be mentioned.

As the therapeutic drug for hyperlipidemia, for example, HMG-CoA reductase inhibitors (e.g., pravastatin, simvastatin, lovastatin, atorvastatin, fluvastatin, lipantil, itavastatin, rosuvastatin or a salt thereof (e.g., sodium salt, calcium salt)), fibrate compounds (e.g., bezafibrate, beclobrate, binifibrate, ciprofibrate, clinofibrate, clofibrate, clofibric acid, etofibrate, fenofibrate, gemfibrozil, nicofibrate, pirifibrate, ronifibrate, simfibrate, theofibrate), squalene synthase inhibitors (e.g., compounds described in WO97/10224, for example, 1-[[(3R, 5S)-1-(3-acetoxy-2,2-dimethylpropyl)-7-chloro-5-(2,3-dimethoxyphenyl)-2-oxo-1,2,3,5-tetrahydro-4,1-benzooxazepin-3-yl]acetyl]piperidine-4-acetic acid), ACAT inhibitors (e.g., avasimibe, eflucimibe), anion exchange resins (e.g., colestyramine), probucol, nicotinic acid drugs (e.g., nicomol, niceritrol), ethyl icosapentate, phytosterol (e.g., soysterol, γ-oryzanol) and the like can be mentioned.

As the antihypertensive drug, for example, angiotensin converting enzyme inhibitors (e.g., captopril, enalapril, delapril), angiotensin II antagonists (e.g., candesartan cilexetil, losartan, eprosartan, valsartan, telmisartan, irbesartan, tasosartan, olmesartan medoxomil, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium antagonists (e.g., manidipine, nifedipine, nicardipine, amlodipine, efonidipine), potassium channel openers (e.g., levcromakalim, L-27152, AL0671, NIP-121), clonidine and the like can be mentioned.

As the antiobesity drug, for example, antiobesity drug acting on the central nervous system [e.g., dexfenfluramine, fenfluramine, phentermine, sibutramine, anfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonists (e.g., CP-422935); cannabinoid receptor antagonists (e.g., SR-141716, SR-147778); ghrelin antagonist; 11β-hydroxysteroid dehydrogenase inhibitors (e.g., BVT-3498)], pancreatic lipase inhibitors [e.g., orlistat, cetilistat (ATL-962)], β3 agonists (e.g., AJ-9677), anorectic peptides [e.g., leptin, CNTF (ciliary neurotrophic factor)], cholecystokinin agonists (e.g., lintitript, FPL-15849), feeding deterrents (e.g., P-57) and the like can be mentioned.

As the diuretic drug, for example, xanthine derivatives (e.g., theobromine sodium salicylate, theobromine calcium salicylate), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzenesulfonamide preparations (e.g., chlorthalidone, mefruside, indapamide), azosemide, isosorbide, ethacrynic acid, piretanide, bumetanide, furosemide and the like can be mentioned.

As the antithrombotic drug, for example, heparin (e.g., heparin sodium, heparin calcium, dalteparin sodium), warfarin (e.g., warfarin potassium), anti-thrombin drugs (e.g., aragatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride and the like) and the like can be mentioned.

Of the above-mentioned concomitant components, biguanides (preferably metformin), insulin secretagogues (preferably sulfonylurea, non-sulfonylurea insulin secretagogues, more preferably glimepiride, nateglinide, mitiglinide or calcium salt hydrate thereof), α-glucosidase inhibitors (preferably voglibose), HMG-CoA reductase inhibitors (preferably simvastatin) and the like are preferable. When using two or more kinds of concomitant components, the combination of biguanide (preferably metformin) and insulin secretagogue (preferably sulfonylurea, more preferably glimepiride) is preferable.

The present invention further provides "a bitter taste suppressing agent of pioglitazone or a salt thereof, which comprises alkali metal chloride" and "use of alkali metal chloride for suppressing the bitter taste of pioglitazone or a salt thereof". Here, as the "alkali metal chloride" and "pioglitazone or a salt thereof", those exemplified as the aforementioned oral preparation of the present invention can be used.

The amount of alkali metal chloride to be used is preferably 1-500 parts by weight, more preferably 2-250 parts by weight, per 100 parts by weight of pioglitazone or a salt thereof.

The above-mentioned bitter taste suppressing agent can remarkably suppress the bitter taste of pioglitazone or a salt thereof in, for example, an "oral preparation containing pioglitazone or a salt thereof" such as the aforementioned oral preparation of the present invention and the like.

The present invention is explained in detail in the following by referring to Reference Example, Examples, Comparative Examples and Experimental Examples, which are not to be construed as limitative.

In the following Reference Example, Examples and Comparative Examples, as the preparation additives (e.g., lactose, D-mannitol, hydroxypropylcellulose, calcium carboxymethylcellulose, crospovidone, magnesium stearate, crystalline cellulose), the Japanese Pharmacopoeia 14th Edition or Japanese Pharmaceutical Excipients 2003 compatible products were used.

EXAMPLES

Reference Example 1

Using pioglitazone hydrochloride, hydroxypropylcellulose, calcium carboxymethylcellulose, lactose and magnesium stearate, and by fluidized bed granulating, milling, and mixing steps, a mixed powder containing pioglitazone hydrochloride (27.6 parts), hydroxypropylcellulose (2.5 parts), calcium carboxymethylcellulose (6 parts), lactose (63.6 parts) and magnesium stearate (0.3 parts) was obtained.

Example 1

Sodium chloride (pulverized in a mortar, and then passed through a 80 mesh sieve, sieved product, average particle size: 90 μm (SYNPATEC HELOS-RODOS particle distribution apparatus), 1.2 g) and the mixed powder (8.0 g) obtained in Reference Example 1 were admixed to give a mixed powder.

Example 2

A mixed powder was obtained in the same manner as in Example 1 except that the amount of sodium chloride was set to 0.8 g.

Example 3

A mixed powder was obtained in the same manner as in Example 1 except that the amount of sodium chloride was set to 0.4 g.

Example 4

To a mixed powder (120 mg) obtained in Reference Example 1 was added 0.9 w/w % sodium chloride aqueous solution (5 mL) and a suspension was obtained.

Example 5

A suspension was obtained in the same manner as in Example 4 except that the concentration of sodium chloride aqueous solution was set to 0.5 w/w %.

Example 6

A suspension was obtained in the same manner as in Example 4 except that the concentration of sodium chloride aqueous solution was set to 0.3 w/w %.

Example 7

Potassium chloride (pulverized in a mortar, and then passed through a 80 mesh sieve, sieved product, average particle size: 98 μm, 1.2 g) and the mixed powder (8.0 g) obtained in Reference Example 1 were admixed to give a mixed powder.

Example 8

A mixed powder was obtained in the same manner as in Example 7 except that the amount of potassium chloride was set to 0.8 g.

Example 9

A mixed powder was obtained in the same manner as in Example 7 except that the amount of potassium chloride was set to 0.4 g.

Example 10

To a mixed powder (120 mg) obtained in Reference Example 1 was added 0.9 w/w % potassium chloride aqueous solution (5 mL) and a suspension was obtained.

Example 11

A suspension was obtained in the same manner as in Example 10 except that the concentration of potassium chloride aqueous solution was set to 0.5 w/w %.

Example 12

A suspension was obtained in the same manner as in Example 10 except that the concentration of potassium chloride aqueous solution was set to 0.3 w/w %.

Example 13

Pioglitazone hydrochloride (47.9 g), crospovidone (Polyplasdone XL-10, ISP JAPAN LTD., 21.7 g), crystalline cellulose (CEOLUS KG-802, Asahi Kasei Chemicals Corporation, 32.6 g) and mannitol (Cat No: 105980, Merck Ltd., Japan, 297.8 g) were charged in a fluidized bed granulator (LAB-1, POWREX CORPORATION), and granulated while spraying a liquid obtained by dissolving or dispersing hydroxypropylcellulose (grade SSL, NIPPON SODA CO., LTD., 3.6 g), yellow ferric oxide (Ansted, 0.5 g) and sodium chloride (8.7 g) in purified water (178.1 g) to give a granulation powder.

The obtained granulation powder (28.5 g), lactose granulation powder (DILACTOSE S, FREUND CORPORATION, 1.2 g) and magnesium stearate (TAIHEI CHEMICAL INDUSTRIAL CO., LTD., 0.3 g) were mixed. The obtained mixed powder was tabletted using Auto-graph (AG-1, Shimadzu Corporation) and a 9 mlφ flat punch having a beveled edge at compression pressure 5.0 (kN/cm$^2$) to give tablets each weighing 0.3 g.

Example 14

A mixture of pioglitazone hydrochloride (80 parts) and crystalline cellulose (CEOLUS PH-101, Asahi Chemical Industry Co., Ltd., 20 parts) was pulverized by a jet mill (PJM-100SP, NIPPON PNEUMATIC MFG. CO., LTD.). The obtained pulverized product (596.1 g, median size of the mixture of pioglitazone hydrochloride and crystalline cellulose: 5 μm), lactose (MEGGLE JAPAN CO., LTD., 581.2 g) and carmellose calcium (ECG-505, GOTOKU CHEMICAL COMPANY LTD., 61.7 g) were charged in tumbling fluidized bed granulating-coating machine (MP-10, POWREX CORPORATION), and granulated while spraying a liquid obtained by dissolving or dispersing hydroxypropylcellulose (grade SSL, NIPPON SODA CO., LTD., 31.9 g) and yellow ferric oxide (Ansted, 0.4 g) in purified water (604 g), and continuously granulated while spraying a liquid obtained by dissolving or dispersing hydroxypropylcellulose (5.6 g) and lactose (210.7 g) in purified water (766 g). The obtained granulation powder was passed through a 30 mesh sieve to give a granulation powder A.

On the other hand, mannitol (Cat No: 105980, Merck Ltd., Japan, 1034.1 g), crystalline cellulose (CEOLUS KG-802, Asahi Chemical Industry Co., Ltd., 162.1 g) and aspartame (Ajinomoto Co., Inc., 162.1 g) were charged in tumbling fluidized bed granulating-coating machine, and granulated with a liquid obtained by dissolving or dispersing mannitol (Cat No: 105980, Merck Ltd., Japan, 67.5 g), sodium chloride (Wako Pure Chemical Industries, Ltd., 202.5 g) and yellow ferric oxide (0.4 g) in purified water (777.5 g). The obtained granulation powder was passed through a 30 mesh sieve to give a granulation powder B.

The granulation powder A (908 g), the granulation powder B (1043 g), crospovidone (Kollidon CL-F, BASF JAPAN LTD., 103.8 g) and magnesium stearate (TAIHEI CHEMICAL INDUSTRIAL CO., LTD., 20.8 g) were mixed. The obtained mixed powder was tabletted using tabletting machine (Cleanpress Correct 19KAWC, KIKUSUI SEISAKUSHO LTD.) and a 9 mmφ flat punch having a is beveled edge at compression pressure 6.3 (kN/cm$^2$) to give tablets each weighing 240 mg.

Example 15

The mixed powder obtained in Example 14 was tabletted using Auto-graph (AG-1, Shimadzu Corporation) and a 7 mmφ flat punch having a beveled edge at compression pressure 6.2 (kN/cm$^2$) to give tablets each weighing 120 mg.

Example 16

The mixed powder obtained in Example 14 was tabletted using Auto-graph (AG-1, Shimadzu Corporation) and a 9.5 mmφ flat punch having a beveled edge at compression pressure 6.9 (kN/cm$^2$) to give tablets each weighing 360 mg.

Comparative Example 1

To a mixed powder (120 mg) obtained in Reference Example 1 was added purified water (5 mL) and a suspension was obtained.

Comparative Example 2

Pioglitazone hydrochloride (59.9 g), crospovidone (Polyplasdone XL-10, ISP JAPAN LTD., 27.2 g), crystalline cellulose (CEOLUS KG-802, Asahi Kasei Chemicals Corporation, 40.7 g) and mannitol (Cat No: 105980, Merck Ltd., Japan, 372.2 g) were charged in a fluidized bed granulator (LAB-1, POWREX CORPORATION), and granulated while spraying a liquid obtained by dissolving or dispersing hydroxypropylcellulose (grade SSL, NIPPON SODA CO., LTD., 4.5 g), yellow ferric oxide (Ansted, 0.6 g) in purified water (86.7 g) to give a granulation powder.

The obtained granulation powder (27.9 g), lactose granulation powder (DILACTOSE S, FREUND CORPORATION, 1.8 g) and magnesium stearate (TAIHEI CHEMICAL INDUSTRIAL CO., LTD., 0.3 g) were mixed. The obtained mixed powder was tableted using Auto-graph (AG-1, Shimadzu Corporation) and a 9 mmϕ flat punch having a beveled edge at compression pressure 5.0 (kN/cm$^2$) to give tablets each weighing 0.3 g.

Comparative Example 3

Five tablets of Pansporin T tablet (Trade name, 100 mg potency as cefotiam), which is a commercially available preparation containing cefotiam hexetil hydrochloride, were pulverized in a mortar, and then passed through a 20 mesh sieve to give a cefotiam hexetil hydrochloride containing mixed powder.

Comparative Example 4

Sodium chloride (pulverized in a mortar, and then passed through a 80 mesh sieve, sieved product, average particle size: 74 μm, 50 mg) and the mixed powder (450 mg) obtained in Comparative Example 3 were admixed to give a mixed powder.

Comparative Example 5

Sodium chloride (pulverized in a mortar, and then passed through a 80 mesh sieve, sieved product, 30 mg) and the mixed powder (570 mg) obtained in Comparative Example 3 were admixed to give a mixed powder.

Experimental Example 1

The bitter taste of pioglitazone hydrochloride was evaluated for the mixed powders obtained in Reference Example and Examples by a functional test using healthy adults. The bitter taste was evaluated according to the following criteria.
1. too bitter to keep it in mouth
2. bitter taste is noted but endurable
3. bitter taste is hardly noted
4. bitter taste is not noted The results are shown in Table 1. The bitter taste in the Table shows average values of n=3.

TABLE 1

| Example | Bitter taste |
|---|---|
| Reference Example 1 | 1 |
| Example 1 | 4 |
| Example 2 | 3 |
| Example 3 | 2.3 |

As shown in Table 1, as compared to the mixed powder of Reference Example 1, the oral preparation (mixed powder) of the present invention remarkably masked the bitter taste of pioglitazone hydrochloride. In other words, using pioglitazone hydrochloride and sodium chloride in combination, the bitter taste of pioglitazone hydrochloride was remarkably masked.

Experimental Example 2

In the same manner as in Experimental Example 1, the suspensions obtained in Comparative Example and Examples were evaluated for the bitter taste of pioglitazone hydrochloride. The results are shown in Table 2. The bitter taste in the Table shows an average value of n=3.

TABLE 2

| Example | Bitter taste |
|---|---|
| Comparative Example 1 | 1.3 |
| Example 4 | 2.7 |
| Example 5 | 2.7 |
| Example 6 | 3.7 |

As shown in Table 2, as compared to the suspension of Comparative Example 1, the oral preparation (suspension) of the present invention remarkably masked the bitter taste of pioglitazone hydrochloride. In other words, using pioglitazone hydrochloride and sodium chloride in combination, the bitter taste of pioglitazone hydrochloride was remarkably masked.

Experimental Example 3

In the same manner as in Experimental Example 1, the mixed powders obtained in Reference Example and Examples were evaluated for the bitter taste of pioglitazone hydrochloride. The results are shown in Table 3. The bitter taste in the Table shows an average value of n=3.

TABLE 3

| Example | Bitter taste |
|---|---|
| Reference Example 1 | 1 |
| Example 7 | 4 |
| Example 8 | 2 |
| Example 9 | 3 |

As shown in Table 3, as compared to the mixed powder of Reference Example 1, the oral preparation (mixed powder) of the present invention remarkably masked the bitter taste of pioglitazone hydrochloride. In other words, using pioglitazone hydrochloride and potassium chloride in combination, the bitter taste of pioglitazone hydrochloride was remarkably masked.

Experimental Example 4

In the same manner as in Experimental Example 1, the suspensions obtained in Comparative Example and Examples were evaluated for the bitter taste of pioglitazone hydrochloride. The results are shown in Table 4. The bitter taste in the Table shows an average value of n=3.

TABLE 4

| Example | Bitter taste |
|---|---|
| Comparative Example 1 | 1 |
| Example 10 | 3.7 |
| Example 11 | 3.7 |
| Example 12 | 3.3 |

As shown in Table 4, as compared to the suspension of Comparative Example 1, the oral preparation (suspension) of the present invention remarkably masked the bitter taste of pioglitazone hydrochloride. In other words, using pioglitazone hydrochloride and potassium chloride in combination, the bitter taste of pioglitazone hydrochloride was remarkably masked.

Experimental Example 5

In the same manner as in Experimental Example 1, one of the tablets obtained in Comparative Example and Example was placed in the mouth, and the bitter taste of pioglitazone hydrochloride was evaluated. The results are shown in Table 5. The bitter taste in the Table shows an average value of n=3.

TABLE 5

| Example | Bitter taste |
|---|---|
| Comparative Example 2 | 1.3 |
| Example 13 | 3.7 |

As shown in Table 5, as compared to the tablet of Comparative Example 2, the oral preparation (tablet) of the present invention remarkably masked the bitter taste of pioglitazone hydrochloride. In other words, using pioglitazone hydrochloride and sodium chloride in combination, the bitter taste of pioglitazone hydrochloride was remarkably masked.

Experimental Example 6

The disintegration time in the oral cavity (time from placing one tablet in the mouth of a healthy adult to its disintegration without chewing) of the tablet obtained in Example 13 was measured. As a result, the time was 30.0 sec (average value of n=3). In addition, the hardness of the tablet obtained in Example 13 was measured using a hardness meter (Toyama Sangyo Co., Ltd.). As a result, the hardness was 40(N).

Experimental Example 7

In the same manner as in Experimental Example 1, the mixed powders obtained in Comparative Examples were evaluated for the bitter taste of cefotiam hexetil hydrochloride. The results are shown in Table 6. The bitter taste in the Table shows an average value of n=3.

TABLE 6

| Example | Bitter taste |
|---|---|
| Comparative Example 3 | 1 |
| Comparative Example 4 | 1 |
| Comparative Example 5 | 1 |

As shown in Table 6, even using cefotiam hexetil hydrochloride and sodium chloride in combination, the bitter taste of cefotiam hexetil hydrochloride could not be masked.

Experimental Example 8

In the same manner as in Experimental Example 1, one of the tablets obtained in Example was placed in the mouth, and the bitter taste of pioglitazone hydrochloride was evaluated. The result is shown in Table 7. The bitter taste in the Table shows an average value of n=3.

TABLE 7

| Example | Bitter taste |
|---|---|
| Example 14 | 4.0 |

As shown in Table 7, the oral preparation (tablet) of the present invention remarkably masked the bitter taste of pioglitazone hydrochloride. In other words, using pioglitazone hydrochloride and sodium chloride in combination, the bitter taste of pioglitazone hydrochloride was remarkably masked.

Experimental Example 9

In the same manner as in Experimental Example 6, the disintegration time in the oral cavity of the tablet obtained in Example 14 was measured. As a result, the time was 29 sec (average value of n=3).

Experimental Example 10

The dissolution property of pioglitazone hydrochloride was evaluated using the tablet obtained in Example 14, and according to the Paddle Method (50 rpm) using pH 2.0 hydrochloric acid-potassium chloride buffer (37° C., 900 mL). As a result, pioglitazone hydrochloride was eluted by 96% in 15 min.

In the same manner as above, the dissolution property of pioglitazone hydrochloride was evaluated after preserving the tablet obtained in Example 14 at 40° C. for 2 months in an air-tight glass bottle. As a result, pioglitazone hydrochloride was eluted by 95% in 15 min.

As demonstrated above, the oral preparation of the present invention (tablet) is superior in the dissolution stability, shows no time-course changes in the dissolution property of pioglitazone hydrochloride.

INDUSTRIAL APPLICABILITY

The oral preparation of the present invention can be administered very easily since the bitter taste of pioglitazone or a salt thereof is sufficiently masked, and therefore, is useful as a pharmaceutical product with high administration compliance of patients. Moreover, the oral preparation of the present invention can be easily produced by combining pioglitazone or a salt thereof and alkali metal chloride.

When the oral preparation of the present invention is an oral preparation rapidly disintegrating in the oral cavity, the preparation is extremely useful as a pharmaceutical product with high administration compliance of patients having difficulty in swallowing pharmaceutical agents, such as the elderly and children, and the like, since the bitter taste of pioglitazone and a salt thereof is sufficiently masked and the preparation has superior disintegratability in the oral cavity.

This application is based on application No. 2006-143390 filed in Japan, the contents of which are incorporated hereinto by reference.

The invention claimed is:

1. An oral preparation in the form of a tablet disintegrating in the oral cavity which comprises (1) coated particles wherein particles comprising pioglitazone or a salt thereof are coated with saccharide, and (2) alkali metal chloride, wherein the weight ratio of pioglitazone or a salt thereof to the alkali metal chloride is 1 to about 0.01-5.

2. The preparation of claim 1, wherein the alkali metal chloride is sodium chloride.

3. The preparation of claim 1, wherein the bitter taste of pioglitazone or a salt thereof is suppressed.

4. The preparation of claim 1, wherein the weight ratio of pioglitazone or a salt thereof to the alkali metal chloride is 1 to about 0.02-2.5.

5. The preparation of claim 1, wherein the median size of pioglitazone or a salt thereof is 0.5 to 25 μm.

6. The preparation of claim 1, wherein the median size of pioglitazone or a salt thereof is 1 to 21 μm.

7. The preparation of claim 1, wherein the median size of pioglitazone or a salt thereof is 1 to 10 μm.

8. A method for suppressing the bitter taste of pioglitazone or a salt thereof, comprising:

forming coated particles comprising pioglitazone or a salt thereof with saccharide;

mixing the coated particles with alkali metal chloride; and compression-molding the obtained mixture to form an oral preparation in the form of a tablet disintegrating in the oral cavity.

9. The method of claim 8, wherein the step of forming coated particles comprising:

forming a granulation product by granulating components comprising pioglitazone or a salt thereof; and coating the granulation product with saccharide.

10. The preparation of claim 1, wherein the saccharide is a sugar alcohol or lactose.

11. The preparation of claim 1, wherein the saccharide is lactose.

12. The preparation of claim 1, which is a solid preparation rapidly disintegrating in the oral cavity in 5 to 90 sec.

\* \* \* \* \*